United States Patent
Chow et al.

(10) Patent No.: US 8,557,038 B2
(45) Date of Patent: Oct. 15, 2013

(54) DUAL-PHASE CALCIUM PHOSPHATE CEMENT COMPOSITION

(75) Inventors: Laurence C. Chow, Potomac, MD (US); Shozo Takagi, Gaithersburg, MD (US)

(73) Assignee: American Dental Association Foundation, Chicago, IL (US)

( * ) Notice: Subject to any disclaimer, the term of this patent is extended or adjusted under 35 U.S.C. 154(b) by 82 days.

(21) Appl. No.: 12/765,150

(22) Filed: Apr. 22, 2010

(65) Prior Publication Data

US 2010/0269736 A1 Oct. 28, 2010

Related U.S. Application Data

(60) Provisional application No. 61/171,691, filed on Apr. 22, 2009.

(51) Int. Cl.
*C04B 12/02* (2006.01)
(52) U.S. Cl.
USPC .......................................... 106/690; 106/35
(58) Field of Classification Search
USPC .................................... 106/690, 35
See application file for complete search history.

(56) References Cited

U.S. PATENT DOCUMENTS

| | | | | |
|---|---|---|---|---|
| 5,149,368 | A * | 9/1992 | Liu et al. ...................... | 424/602 |
| 5,262,166 | A | 11/1993 | Liu et al. | |
| 5,522,893 | A | 6/1996 | Chow et al. | |
| 5,525,148 | A | 6/1996 | Chow et al. | |
| 6,325,992 | B1 | 12/2001 | Chow et al. | |
| 6,547,866 | B1 * | 4/2003 | Edwards et al. ............ | 106/35 |
| 6,616,742 | B2 * | 9/2003 | Lin et al. .................... | 106/35 |
| 6,642,285 | B1 | 11/2003 | Bohner | |
| 6,793,725 | B2 * | 9/2004 | Chow et al. ................ | 106/35 |
| 7,186,294 | B2 * | 3/2007 | Lin et al. .................... | 106/690 |
| 7,201,797 | B2 * | 4/2007 | Lin et al. .................... | 106/690 |
| 7,294,187 | B2 * | 11/2007 | Chow et al. ................ | 106/35 |
| 7,416,602 | B2 * | 8/2008 | Murphy et al. ............. | 106/690 |
| 7,459,018 | B2 * | 12/2008 | Insley et al. ................ | 106/690 |
| 7,473,312 | B2 | 1/2009 | Barralet et al. | |
| 7,709,029 | B2 * | 5/2010 | Chow et al. ................ | 424/602 |
| 8,216,359 | B2 * | 7/2012 | Lee, et al. .................. | 106/690 |
| 2006/0096504 | A1 * | 5/2006 | Grover et al. .............. | 106/691 |
| 2006/0213398 | A1 * | 9/2006 | Barralet et al. ............ | 106/690 |
| 2006/0225620 | A1 * | 10/2006 | Murphy et al. ............. | 106/690 |
| 2007/0092580 | A1 * | 4/2007 | Chow et al. ................ | 424/602 |
| 2007/0186818 | A1 * | 8/2007 | Bohner ....................... | 106/691 |
| 2008/0028992 | A1 * | 2/2008 | Lee et al. .................... | 106/690 |
| 2010/0212545 | A1 * | 8/2010 | Chow et al. ................ | 106/35 |
| 2010/0313791 | A1 * | 12/2010 | Chen et al. ................. | 106/690 |
| 2011/0224675 | A1 * | 9/2011 | Tofighi et al. ............. | 606/94 |

FOREIGN PATENT DOCUMENTS

WO 2004093734 A2 11/2004

OTHER PUBLICATIONS

Sarda, et al., Wiley Periodicals, Inc., "Kinetic Study of Citric Acid Influence on Calcium Phosphate Bone Cements as Water-Reducing Agent", 2002, pp. 653-659.
Yoshikawa, et al., John Wiley & Sons, Inc., "Reconstruction of Alveolar Bone Defect by Calcium Phosphate Compounds". 2000, pp. 430-437.
Takechi et al., Elsevier Science Ltd. Biomaterials, "Initial Histological Evaluation of Anti-Washout Type Fast-Setting Calcium Phosphate Cement Following Subcutaneous Implantation", 1998, pp. 2057-2063.
Hannink et al., Wiley Periodicals, Inc., "In Vivo Behavior of a Novel Injectable Calcium Phosphate Cement Compared with Two Other Commercially Available Calcium Phosphate Cements", 2007, pp. 478-488.
Chow et al., Materials Research Society, "Self-Setting Calcium Phosphate Cements", 1991, vol. 179, pp. 3-24.
Chow, The Centennial Memorial Issue of the Ceramic Society of Japan, "Development of Self-Setting Calcium Phosphate Cements", 1991, pp. 954-964.
Ishikawa et al., Dent Mater, "Behavior of a Calcium Phosphate Cement in Simulated Blood Plasma in Vitro", Jan. 1994, pp. 26-32.
Chow et al., John Wiley & 'Sons, Inc., "Diametral Tensile Strength and Compressive Strength of a Calcium Phosphate Cement: Effect of Applied Pressure", 2000, pp. 511-517.
Stryker HydroSet Injectable HA Bone Substitute, "The Latest Advancement in Bone Substitute Technology", 2006, pp. 1-6.
Notification of Transmittal of the International Search Report and the Written Opinion of the International Search Authority, or the Declaration of PCT/US10/32084 mailed Jul. 26, 2010.

* cited by examiner

*Primary Examiner* — Paul Marcantoni
(74) *Attorney, Agent, or Firm* — Banner & Witcoff, Ltd

(57) ABSTRACT

Disclosed are dual-phase cement precursor systems and associated methods and kits. The cement precursor systems comprises at least first and second phases each containing a calcium phosphate compound. When mixed, the first and second cement precursor phases form a biocompatible cement. The disclosed systems include an organic acid in an amount effective to enhance the working time of the cement precursor composition, and also include a setting accelerator. In some embodiments, one or more of the calcium phosphate compounds is provided in the form of particles with a nonmonomial particle sized distribution.

6 Claims, No Drawings

DUAL-PHASE CALCIUM PHOSPHATE CEMENT COMPOSITION

CROSS REFERENCE TO RELATED APPLICATIONS

This is a utility application claiming priority to and incorporating by reference provisional application entitled DUAL-PHASE CALCIUM PHOSPHATE CEMENT COMPOSITION, Ser. No. 61/171,691 filed Apr. 22, 2009.

STATEMENT OF FEDERALLY SPONSORED RESEARCH

The invention was made in the course of research supported at least in part by Grant DE11789 from the National Institute of Dental and Cranial Facial Research and carried out at the National Institute of Standards and Technology. The U.S. Government may have certain rights to the invention.

TECHNICAL FIELD

Generally, the invention is in the field of cements that are useful in connection with bone repair procedures. Preferred embodiments of the invention provide dual-phase cement precursor systems in which the cement precursors take the form of first and second precursor phases. The phases initially are separate, but a cement suitable for bone repair procedures may be formed upon blending of the first and second phases.

BACKGROUND OF THE INVENTION

Several types of self-hardening calcium phosphate compositions have been studied (Brown and Chow, A New Calcium Phosphate Water Setting Cement, pp. 352-379 in Brown, *Cements Research Progress*, American Ceramic Society, OH, 1986; Ginebra et al., Setting Reaction and Hardening of an Apatitic Calcium Phosphate Cement, *J. Dent. Res.* 76:905-912, 1997; Constantz et al., Histological, Chemical, and Crystallographic Analysis of Four Calcium Phosphate Cements in Different Rabbit Osseous Sites, *J Biomed Mater. Res. [Appl. Biomater.]* 43:451-461, 1998; Miyamoto et al., Histological and Compositional Evaluations of Three Types of Calcium Phosphate Cements When Implanted in Subcutaneous Tissue Immediately After Mixing, J. *Biomed. Mater. Res. [Appl. Biomater]* 48:36-42, 1999; Lee et al., Alpha-BSM (R): A Biomimetic Bone Substitute and Drug Delivery Vehicle, *Clin. Orthop Rel. Res.* 367:396-405, 1999. Because of its chemical and crystallographic similarity to the carbonated apatitic calcium phosphate mineral found in human bones and teeth, hydroxyapatite has been one of the most often used restorative materials for the repair of human hard tissues One of the calcium phosphate compositions, developed by Brown and Chow in 1986 and named calcium phosphate cement, or CPC, self-hardens to form hydroxyapatite as the primary product. The term "self-harden" refers to the paste being able to harden by itself. For example, the CPC paste can be placed into a bone cavity, and can self-harden after contact with an aqueous medium. CPC typically may be composed of particles of tetracalcium phosphate (TTCP: $Ca_4(PO_4)_2O$) and dicalcium phosphate anhydrous (DCPA: $CaHPO_4$) that react in an aqueous environment to form solid hydroxyapatite, Ishikawa et al., Reaction of Calcium Phosphate Cements with Different Amounts of Tetracalcium Phosphate and Dicalcium Phosphate Anhydrous, *J. Biomed. Mater. Res.* 46:504-510, 1999; Matsuya et al., Effects of Mixing Ratio and Ph on The Reaction Between $Ca_4[PO_4]_2O$ and $CaHPO_4$, *J. Mater. Sci.: Mater. in Med.* 11:305-311, 2000; Takagi et al., Morphological and Phase Characterizations of Retrieved Calcium Phosphate Cement Implants, *J. Biomed. Mater. Res. [Appl. Biomater.]*58:36-41, 2001. Calcium phosphate compositions (such as CPC) are highly promising for a wide range of clinical uses due to their excellent biocompatibility, osteoconductivity and bone replacement capability. For example, CPC has been studied for use in the reconstruction of frontal sinus and augmentation of craniofacial skeletal defects (Shindo et al., Facial Skeletal Augmentation Using Hydroxyapatite Cement, *Arch. Otolaryngol. Head Neck Surg.*, 119:185-190, 1993), endodontics (Sugawara et al., In vitro Evaluation of the Sealing Ability of a Calcium Phosphate Cement When Used as a Root Canal Sealer-Filler, *J. Endodont.* 16:162-165, 1990), and root canal applications (Chohayeb et al., Evaluation of Calcium Phosphate as a Root Canal Sealer-Filler Material, *J. Endodont.* 13:384-387, 1987).

Most of the presently available calcium phosphate cements are mixed with an aqueous solution prior to use. Accordingly, the ability of the surgeon to properly mix the cement and then place the cement paste into a bone defect within the prescribed time prior to cement hardening is a crucial factor in achieving optimum results. The art thus has recognized the desirability of providing pre-mixed cement pastes that are stable as provided but that harden only after being introduced to the bone defect and positioned appropriately. Pre-mixed self-hardening cements may be formulated by combining glycerol, sodium phosphate, hydroxypropyl methyl cellulose and calcium phosphate cement powders, as described in Takagi et al., "Properties of premixed calcium phosphate cement pastes," *J. Biomed Mater Res. [Applied Biomater]* 67B:689-696 (2003). The hydroxypropyl methyl cellulose and sodium phosphate used in such pastes are believed to improve paste cohesiveness and accelerate cement hardening, respectively. The hardening times of the forgoing cements are about 60 minutes, which is much longer then 5- to 30-minute setting time desired in many cases.

To provide stability, the heretofore described cements are formulated as non-aqueous pre-mixed materials. Cement hardening does not begin until these precursors are placed into a bone defect, whereupon water from surrounding tissues enters into the cement. These cements, while often possessing excellent physical properties, sometimes can be limited in utility. Cement hardening in the interior of the cement mass may be slow under some clinical bone grafting conditions, for instance, wherein the amount of water available from the tissues is limited, or wherein the interior of the cement is more than several millimeters away from the nearest graft-tissue interface. Additionally, such cements typically are required to be formulated to be able to react extremely rapidly when exposed to moisture. Such formulations typically do not have a long shelf life, in light of the difficulties inherent in excluding moisture during manufacture and storage.

Co-pending U.S. patent application Ser. No. 11/550,586 contains excellent teachings as to dual-phase cement precursor systems. In this application, a number of such systems are disclosed. With respect to the calcium phosphate cements described therein, it has been found under some circumstances that the working time of a cement prepared upon mixing of the first and second phases is less than is sometimes desired. Generally, the compositions described therein may be provided in the form of a kit that includes the first and second phases (usually contained in separate containers) and a dispenser device. As set forth more detail therein, a suitable dispensing device may include a dual-barrel microdispenser (1:1 volume ratio) equipped with a static mixing and a delivery tip. The first and second phases are mixed in the static mixer and dispensed onto a surface, such as a surface in need of bone repair. It is desirable for the cement composition thus formed to remain workable and manually manipulable by a surgeon for a period of time of at least 30 seconds, and preferably one minute, and more preferably two minutes or longer, after dispensing and before the composition sets up to the point of no longer being manually manipulable. Some of the calcium phosphate cement compositions described in the heretofore indicated application, while useful as dual-phase cement precursor compositions, are not believed to provide such a working time.

SUMMARY

The invention provides, in various embodiments, dual-phase cement precursor compositions, methods for bone repair, and kits. In some embodiments, dual-phase cement precursor compositions include first and second calcium phosphate compounds and an organic acid. The first and second calcium phosphate compounds are present in discrete phases. At least one of the phases is provided with an organic acid, or salt of such organic acid, in an amount effective to increase the working time of the cement composition formed upon mixing the two phases. The composition further is provided with a setting accelerator, which in some embodiments is a calcium phosphate salt. A setting accelerator in an amount effective to decrease the time in which the cement composition hardens.

In the course of some embodiments, a kit includes first and second phases of a dual-phase cement precursor composition as discussed above. The first and second phases are provided as separate materials, generally as pastes disposed respectively in first and second containers. The kit further is provided with a dispenser device, which, in some embodiments is a microdispenser equipped with a static mixing tip.

Also provided in some embodiments of the invention is a method for bone repair. Generally, in these embodiments, the method comprises providing a composition as described herein, and applying a blend of first and second phases to an area where bone repair is desired. In such embodiments, it is intended that the blended phases will provide a calcium phosphate cement that is workable for a sufficient period of time to allow manual manipulation by the surgeon for at least 30 seconds after the blend is dispensed. The cement thus formed is biocompatible and is believed suitable for bone repair.

DETAILED DESCRIPTION

The cements that may be prepared from the cement precursors in accordance with the present invention are useful in connection with bone repair, by which is contemplated any bone grafting or other procedure used to correct defective or incorrectly formed bones, damages bones, and the like. The bone repair procedure may be performed in any animal, such as a human.

It is contemplated that a cement is a material that will set up, or harden, over a period of ninety minutes or less, when the cement is used at room temperature (20-25° C.). Cement precursors are materials that in ordinary use themselves are not cements, but that may be blended with another precursor to form a cement. The cement precursors are provided in the form of a dual-phase cement precursor system, by which is contemplated a system that includes at least two (but optionally additional) precursor phases. Each of the phases comprises a compound or composition, and each phase in the dual-phase system is different from at least one other phase in the system. The phases themselves are not cements, in that the phases themselves do not set to form a hard material in ordinary use. Rather, when the phases are combined, a cement is formed thereby.

The system generally includes the two phases, which may be provided together in a container that is equipped to keep the phases separate until use. Any suitable container may be used in conjunction with the invention, and thus, for instance, the container may be any appropriate box, or bag, or package. In some cases, the container may be an appropriately configured syringe. The container may contain separate vials for the precursor phases, or separate compartments for the phases.

Preferably, the system is provided in the form of a kit, the kit including the dual phase cement precursor system and an appropriate mixing device. The mixing device may be conventional, or may otherwise be a device suitable for use in conjunction with the cement precursor systems taught. The prior art has provided a microdispenser with a static mixing tip, the mixing tip comprising an auger-like structure that allows the two phases to be blended rapidly and subsequently to be applied to the desired area. An example of such a device is the Dual-barrel 9 mL Micro Dispensing System by Tah Industries, Robinsville, N.J. The invention contemplates the use of this device, or an analogous device that is specifically designed for medical usage. In some embodiments, the microdispensers may include a region that serves as the container for the phases, by providing separate holding chambers for the first and second phases.

Each phase preferably is sufficiently stable to permit transport and reasonable storage prior to use. Stability may be measured by any technique or using any criteria deemed appropriate. In accordance with one such technique, a sample of the material or materials constituting the phase is heated to a temperature of 50° C., and held at this temperature for seven days. The material then is used in the formation of a cement, and the setting time of the cement is evaluated as compared with the original setting time of a similar cement made without thermal treatment of either of the phases. If the setting time of the cement made with the thermally treated phase is approximately equal to the setting time of the similar cement, the phase may be deemed suitably stable for use in conjunction with the present invention. The invention is not limited to cement precursor systems that meet this criterion; rather, the foregoing is provided to illustrate one of but many possible methods for evaluating stability.

The phases themselves may be in any suitable form. In some embodimen ts, one of the phases is aqueous, and the other contains a liquid (at room temperature) and is substantially nonaqueous. The water present in the aqueous phase generally should be present as liquid water, although it is contemplated in some embodiments that water may be present solely in the form of hydrates of solid materials. The other phase may be an aqueous phase, if an aqueous phase would be suitably stable for the other materials in the phase. By "substantially non-aqueous" is contemplated that essentially no hydrated or liquid water is present in the phase. It is contemplated that in a substantially non-aqueous phase there will be trace amounts of moisture present, such as moisture that is unavoidably present notwithstanding reasonably prudent steps to exclude such moisture. In some embodiments, a liquid non-aqueous phase is provided. The liquid can be any suitable room temperature liquid, examples of which include glycerin, ethanol, propanol, certain polyethylene glycols, and propylene glycol. Glycerin is deemed particularly preferred, in light of its biocompatibility and complete miscibility with water.

Each phase includes one or more calcium phosphate compounds. Exemplary calcium compounds suitable for use in conjunction with the invention include tetracalcium phosphate (TTCP), dicalcium phosphate anhydrous (DCPA), dicalcium phosphate dihydrate (DCPD), alpha-tricalcium phosphate (alpha-TCP), beta tricalcium phosphate (beta-TCP), hydroxyapatite (HA), amorphous calcium phosphate (ACP), octacalcium phosphate (OCP), calcium deficient hydroxyapatite, carbonate-containing hydroxyapatite (CHA), fluoride-containing hydroxyapatite (FHA), calcium lactate, calcium sulfate, calcium gluconate, calcium lactate gluconate, calcium glycerophosphate, calcium silicate, calcium hydroxide, and other biocompatible calcium compounds. Generally, calcium compounds that are biocompatible and that form a suitable cement may be used. The calcium phosphate compounds may be present in any suitable amount in the paste, for example, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% by total weight of the paste. When two or more calcium phosphate compounds are used in a single paste, they may be used in any suitable amounts relative to one another.

In forming a cement, the phases may be blended in any suitable amounts. When each phase is a liquid, preferably the phases are formulated such that the volumetric ratio of mixing ranges from 0.1-10, more preferably, 0.25-4. Any suitable calcium phosphate compounds may be used in the respective first and second phases, and many of the heretofore discussed calcium compounds are deemed particularly suitable. Generally, it is preferred that the Ca/P ratio ranges from 0.5 to 2.0 in each phase. In some embodiments, particularly when it is desired to form hydroxyapatite, one of the phases includes a calcium phosphate in which the Ca/P ratio is less than 5/3, and the other includes a calcium phosphate compound in which the Ca/P ratio is greater than 5/3. The Ca/P ratio in hydroxyapatite is 5/3, and it is believed that providing calcium and phosphate in both greater and lesser amounts will drive formation of hydroxyapatite.

One or both of the pastes preferably further includes an organic acid or salt thereof. Any suitable organic acid may be used, but in some embodiments the acid is succinic or citric acid. The acid or salt should be present in an amount effective to increase the working time of the biocompatible cement formed upon mixing relative to the working time to a similar cement prepared in the absence of the organic acid or salt. Although it is not intended to limit the invention to a particular theory of operation, it is believed that the acid will delay the formation of a calcium phosphate complex.

One or both of the pastes, but preferably the aqueous paste, contains a setting accelerator. The setting accelerator may be any suitable material that effective in accelerating the setting of the composition relative to the same composition absent the setting accelerator. In some embodiments, the setting accelerator is a calcium phosphate composition, such as monocalcium phosphate anhydrous (MCPA) or monocalcium phosphate monohydrate (MCPM). The setting accelerator preferably is soluble in the aqueous paste and is present at saturation levels. While not wishing to be bound by a particular theory of operation, it is believed that the setting accelerator will precipitate and will cause nucleation. The setting accelerator is believed to promote acceleration despite the presence of the carboxylic acid. It is believed that the effect of the carboxylic acid increases the working time via a mechanism that is different from the mechanism of the setting accelerator. The setting accelerator may be present in any suitable amount, for instance, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% by total weight of the paste.

In many embodiments, one or both of the cement precursor compositions includes a gelling agent. The gelling agent is a compound or composition that increases the viscosity of the composition and causes the composition to take the form of a gelled or gel-like paste, with at least some of the calcium phosphate compounds present as suspended solids. It is not necessary that the gelling agent cause the formation of a chemical gel. Any suitable gelling agent may be used. In many embodiments, the gelling agent is hydroxyethyl cellulose. The gelling agent may be present in any suitable amount, for instance, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% by total weight of the paste.

The nature and number of compounds and functional materials present in the cements is not limited to the heretofore described ingredients, but to the contrary any other suitable osteoconductive, bioactive, bioinert, or other functional materials may be used in conjunction with the invention. When used, these optional ingredients, may be present in any amounts suitable for their intended purposes.

For instance, in some embodiments, one of the cement precursors includes an osteoinductive protein, by which is contemplated any protein that is useful in assisting in or inducing bone formation. Osteoinductive proteins are deemed particularly suitable for use in conjunction with the carboxyl/calcium cement systems because, at least for many known osteoinductive proteins, such proteins may denature at an alkaline pH.

Another optional ingredient is a filler, such as a radio opaque filler. The radio opaque filler may, for instance, be a suitable bismuth, barium, or iodide compound, such as barium sulfate or bismuth hydroxide. Other suitable fillers include bioglass, silicas, alumina, biphasic calcium phosphate, calcium silicate, calcium sulfate, granular calcium phosphate ceramics, Portland cement, and the like.

A medicament, such as zinc, magnesium, or any other suitable medicament may be included in one or both of the phases of the cement precursors.

In some embodiments, a macropore forming material may be used. As disclosed, for instance, in prior U.S. Pat. Nos. 7,018,460 and 6,955,716, a macropore forming material, such as mannitol, is useful in forming a macropores, or pores having a size greater than 150 microns. Such pores are sometimes deemed desirable and that they create a structure that may be useful in promoting growth of soft tissue in or near the region of these cements.

Also as described in prior U.S. Pat. Nos. 7,018,460 and 6,955,716, in some embodiments, one or more strength-enhancing components, such as fibers, meshes, or the like, may be used. Such components may be resorbable or non-resorbable.

The following Examples are provided to illustrate the invention, but should not be construed as limiting the invention in scope. All of these Examples describe dual-phase cement precursor systems in which two liquid pastes were prepared, the pastes being denoted as Paste 1 and Paste 2.

EXAMPLE 1

A kit was prepared using the following pastes and a dispensing device. Equal volumes of Paste 1 and Paste 2 were mixed in the device and applied to a surface.

| | Material | Weight (g) | % w/w |
|---|---|---|---|
| PASTE 1 | MCPM | 10 | 11.42 |
| | DCPA | 50 | 57.08 |
| | Water | 21.23 | 24.24 |
| | Citric Acid Monohydrate | 5.51 | 6.29 |
| | Tri-Sodium Citrate DiHydrate | 0.58 | 0.66 |
| | Natrosol 250Pharm HHX | 0.28 | 0.32 |
| PASTE 2 | TTCP HS | 48 | 57.83 |
| | TTCP BS | 12 | 14.46 |
| | Propylene Glycol | 23.74 | 27.40 |
| | Natrosol 250Pharmm HHX | 0.26 | 0.31 |

Paste volume ratio 1:1

The cements consisted of two premixed pastes. Paste 1 consisted of monocalcium phosphate monohydrate (MCPM, $Ca(H_2PO_4)_2 2H_2O$, (as received, Spectrum Chemical MFG Corp., New Brunswick, N.J.) mixed with 2 mol/L citric acid solution (sigma-Aldrich Inc., St. Louis, Mo.). Paste 2 consisted of fine tetracalcium phosphate (TTCPF), median size 3.95±0.12 μm (n=4), and medium TTCP (TTCPM), median size 20.41±0.21 μm (n=4), mixed glycerin.

| | TTCPF mass fraction | paste1/paste2 | setting time |
|---|---|---|---|
| Example 2 | 0.07 | 1/1 | 3 ± 1* |
| Example 3 | | 1/2 | 5 ± 1 |
| Example 4 | | 1/4 | 8 ± 1 |
| Example 5 | 0.14 | 1/1 | 1 ± 1 |
| Example 6 | | 1/2 | 2 ± 1 |
| Example 7 | | 1/4 | 3 ± 1 |
| C. E. 1 | 0.33 | any ratio | too fast to measure |

*mean ± s.d., n = 3

The cements consisted of two premixed pastes. Paste 1 consisted of 5 g of monocalcium phosphate monohydrate (MCPM) mixed with approximately 2.2 g of a citric acid solution of varying concentrations of 1.8, 2.3, 3.0, and 3.5 mol/L. Paste 2 consisted of 0.35 g of TTCOF and 4.65 g of TTCPM mixed with appropriately 2.4 g of a glycerin solution. Equal mass of the two pastes were combined and thoroughly mixed. The cement work time has defined as the length of time during which the mixed paste can be molded into desired shapes without the danger of destroying the ability of the paste to set into a hard mass subsequently. The cement hardening time was measured by Gilmores needle as before. As shown in the examples below, both the work time and hardening time were directly affected by the citric acid concentration in paste 1.

| | Citric acid concentration mol/L | Work time, min | Hardening time, min |
|---|---|---|---|
| Ex. 8 | 1.8 | 2.2* | 4.5 |
| Ex. 9 | 2.3 | 2.8 | 6.0 |
| Ex. 10 | 3.0 | 4.0 | 7.5 |
| Ex. 11 | 3.5 | 6.0 | 9.0 |

*mean value in minutes (n ≥ 2); s.d. ≈ 1 min in call cases

| | | 2.0 ml | | 2.75 mol/L | | 3.5 mol/L | |
|---|---|---|---|---|---|---|---|
| | DCPD/MCPM | work time | set time | work time | set time | work time | set time |
| Ex. 12 | 0/100 | 1.5+ | 3 | 2.8 | 7 | 7.3 | 9 |
| Ex. 13 | 25/75 | 1.3 | 4 | 3.5 | 6 | 8 | 12 |
| Ex. 14 | 50/50 | 3.5 | 13 | 3.8 | 9 | 7.5 | 15 |
| Ex. 15 | 75/75 | 3.8 | 21 | 4.5 | 9 | 10 | 26 |

*mean value in minutes (n ≥ 2); s.d. ≈ 1 min in call cases

It is thus seen that the present invention provides, in various embodiments, dual-phase cement precursor systems and related kits and methods. When injected, blending of the first and second phases is caused during injection to form a biocompatible cement that is workable for a period of time sufficient to permit manual manipulation by the surgeon. Through modification of the cement chemistry and formulation, a wide range of properties may be realized.

All references, including publications, patent applications, and patents, cited herein are hereby incorporated by reference. In any listing of possible ingredients or components, mixtures of the possible ingredients or components are contemplated unless expressly indicated otherwise. The description of certain embodiments as "preferred" embodiments, and other recitation of embodiments, features, or ranges as being preferred, is not deemed to be limiting, and the invention is deemed to encompass embodiments that are presently deemed to be less preferred. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. For instance, the heretofore described parameters for evaluating the stability of a precursor phase are not deemed to be limiting, unless otherwise specified in the claims. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. The description herein of any reference or patent as "prior" is not intended to constitute a concession that such reference is available as prior art against the present invention.

What is claimed is:

1. Dual-phase cement precursor compositions for forming a bone repair cement upon mixing for implantation, molding and manipulation during a work time, subsequent setting and hardening comprising:
   first and second discrete unmixed phases, each phase in the form of a paste which is not by itself capable of forming a cement, said first phase being aqueous and comprising a first calcium phosphate compound selected from the group consisting of dicalcium phosphate anhydrous, dicalcium phosphate dihydrate, or mixtures thereof and said second phase being non-aqueous and comprising tetracalcium phosphate, said first and second phases forming a biocompatible cement upon mixing, said first phase including an organic acid or salt thereof selected from the group consisting of citric acid, succinic acid, and mixtures of the foregoing in an amount effective to increase the work time of the biocompatible cement formed upon mixing relative to the work time to a similar cement prepared in the absence of said organic acid or salt thereof, said first phase further comprising a setting accelerator selected from the group consisting of monocalcium phosphate monohydrate and monocalcium phosphate anhydrous, said phases characterized upon mixing to allow manual forming and manipulation during a work time of about at least 30 seconds to about 10 minutes and subsequent setting and hardening.

2. Dual-phase cement precursor compositions according to claim 1, at least one of said first and second phases including a gelling agent.

3. Dual-phase cement precursor compositions according to claim 2, each of said first and second phases including a gelling agent.

4. Dual-phase cement precursor compositions according to claim 2, said gelling agent comprising hydroxyethyl cellulose.

5. Dual-phase cement precursor compositions according to claim 1, said first phase paste including a calcium phosphate compound selected from the group consisting of dicalcium phosphate anhydrous, dicalcium phosphate dehydrate, and mixtures thereof, said second phase comprising tetracalcium phosphate, at least one of the forgoing calcium phosphate compositions being provided in the form of particles, each said first and second phase paste having a calcium/phosphate (Ca/P) ratio in the range of 0.5 to 2.0 and said first phase paste organic acid comprising citric acid in an amount of about 3% to about 23%.

6. Dual-phase calcium phosphate compositions according to claim 1, said first phase comprising:
water;
dicalcium phosphate anhydrous;
monocalcium phosphate monohydrate;
citric acid or a salt thereof; and
hydroxyethyl cellulose;
said second phase comprising:
tetracalcium phosphate in the form of particles having a non-monomodal particle size distribution;
propylene glycol; and
hydroxyethyl cellulose.

* * * * *